United States Patent [19]

Martini et al.

[11] Patent Number: 5,110,390
[45] Date of Patent: May 5, 1992

[54] METHOD OF MAKING A LAMINATE

[75] Inventors: Francesco Martini, Rho; Luigi Perazzo, Cuneo, both of Italy

[73] Assignee: W. R. Grace & Co.-Conn., Duncan, S.C.

[21] Appl. No.: 420,449

[22] Filed: Oct. 12, 1989

Related U.S. Application Data

[60] Division of Ser. No. 342,595, Apr. 21, 1989, Pat. No. 4,906,495, which is a continuation of Ser. No. 136,679, Dec. 21, 1987, abandoned.

[30] Foreign Application Priority Data

Dec. 24, 1986 [GB] United Kingdom ............. 8630963

[51] Int. Cl.$^5$ ............................. B29B 47/06
[52] U.S. Cl. ............................. 156/244.11; 428/35.5; 428/36.7; 428/215; 428/349; 428/516; 428/349; 428/910; 604/332; 604/333; 604/338
[58] Field of Search ............ 156/244.11; 428/35.5, 428/36.7, 215, 286, 349, 516, 910, 347; 264/209.5, 514, 210.5; 604/332, 333, 338

[56] References Cited

U.S. PATENT DOCUMENTS

| 3,546,716 | 12/1970 | Laumann | 4/452 |
|---|---|---|---|
| 3,661,695 | 5/1972 | Berliner | 428/215 |
| 4,372,311 | 2/1983 | Potts | 428/507 |
| 4,469,728 | 9/1984 | Belz | 156/244.11 |
| 4,490,145 | 12/1984 | Campbell | 604/333 |
| 4,561,920 | 12/1985 | Foster | 156/244.11 |
| 4,868,024 | 9/1989 | Cross et al. | 604/332 |
| 4,880,592 | 11/1989 | Martini et al. | 264/209.5 |
| 4,892,603 | 1/1990 | Lustig et al. | 156/244.11 |
| 4,946,720 | 8/1990 | Oishi et al. | 604/332 |

FOREIGN PATENT DOCUMENTS

| 0010171 | 4/1980 | European Pat. Off. |
| 23701 | 2/1981 | European Pat. Off. |
| 30091 | 6/1981 | European Pat. Off. |
| 142950 | 5/1985 | European Pat. Off. |
| 0142950 | 5/1985 | European Pat. Off. |
| 0226439 | 6/1987 | European Pat. Off. |
| 1544780 | 4/1979 | Fed. Rep. of Germany |
| 1384791 | 2/1973 | United Kingdom |
| 1348660 | 3/1974 | United Kingdom |
| 2083762B | 2/1985 | United Kingdom |
| 84/01988 | 5/1984 | World Int. Prop. O. |

Primary Examiner—Caleb Weston
Attorney, Agent, or Firm—John J. Toney; William D. Lee, Jr.; Mark B. Quatt

[57] ABSTRACT

Laminated sheet material 9 comprises a laminate of a polyvinyl alcohol or other water-disintegratable film 12 with a thin coextruded film comprising a melt-bondable layer 15 and an impermeable layer 14. The laminate is odor impermeable but water disposable and so can be used to form a toilet-disposable ostomy bag by melt-sealing around the edges 10 between the facing melt-sealable surfaces 15.

5 Claims, 1 Drawing Sheet

METHOD OF MAKING A LAMINATE

This is a divisional application of application Ser. No. 342,595, filed on Apr. 21, 1989, now U.S. Pat. No. 4,906,495, which is a continuation of Ser. No. 136,679 filed Dec. 21, 1987, now abandoned.

This invention relates to plastic films suitable for use in articles that are to retain body excretions. It also relates to the articles made from such films, and in particular to ostomy bags and films from which they can be made.

It is well known to collect body excretions in an article comprising a plastic film. For instance a bedpan may be provided with a liner comprising a plastic film a diaper may be provided with a plastic backsheet or an ostomy bag may be formed from the film. The film must be impermeable to water during use, as otherwise leakage will occur during use. The film must be resistant to physical damage. If the film is made wholly from water insoluble material to a thickness that will give it sufficient physical strength, the disposal of the used article in a conventional toilet system incurs the risk of blockage of the system.

In U.S. Pat. No. 3,546,716 a bedpan liner is formed of a laminate of a polyvinyl alcohol backsheet, a paraffin- or wax- impermeable layer and a paper tissue cover layer. In U.S. Pat. No. 3,661,695 a bedpan liner or bag is formed of a laminate of, for instance, two films of polyvinyl alcohol adhered by an impermeable adhesive layer. Unfortunately neither of these systems gives an adequate combination of physical strength, liquid impermeability and odour impermeability. It is, for instance, essential that there should be substantially no escape of odours from within an ostomy bag.

In U.S. Pat. No. 4,372,311 an article is made by coating a film of water soluble polymer with a thin layer of biodegradable water insoluble polymer, generally by application of a solution of the insoluble polymer.

In GB 2,083,762 an ostomy bag is formed of an outer layer of water soluble polymer and an inner water impermeable layer that can be of polyvinylidene chloride (PVDC), greases or various other materials. Again this layer is, in all the detailed description, made by coating the water soluble film with a solution of the impermeable material. The patent recognises that the resultant impermeable layer is very thin and warns that it will probably be too thin to provide an effective edge bond, and that it is therefore desirable to terminate the coating short of the edge of the ostomy bag, in order that the water soluble polymer layers can be in direct contact with one another. The use of heat sealing for the edge bonding is mentioned.

Although both these patents emphasise forming the impermeable layer by coating from a solution they both mention the possibility of laminating a pre-formed sheet of a water insoluble polymer to the water soluble polymer film (U.S. Pat. No. 4,372,311 column 2 line 36 and GB 2,083,762B page 4 line 8). Such sheets will inevitably be relatively thick and so will introduce disposal problems and this is probably why neither patent describes in detail the use of such sheets. Instead they both concentrate on forming the impermeable layer by coating methods. Unfortunately these coating methods inevitably result in layers that are intended to be impermeable but which do contain sufficient flaws to create serious problems in practice. These flaws result in odour permeability which is too high and, often, sufficient escape of urine or other liquids to attack the outer, water soluble, support layer. Accordingly they have proved unsatisfactory in practice and so at present ostomy bags are still made from preformed films of, e.g., PVDC that are thicker and less easily disposable than is desirable.

A large number of other laminates have been proposed in the literature. Examples are in GB 1,348,660 and EP 10171. However none have proved capable of meeting the required combination of toilet disposability with reliable impermeability and other physical properties.

It has therefore been our object to provide laminated sheet materials that have this combination of properties and, in particular, to provide materials, and articles such as ostomy bags, that have good odour and liquid impermeability and that can easily be disposed of in conventional toilet systems, without blockage of the systems.

A laminated sheet material according to the invention comprises a laminate of (a) a water-disintegratable film, and (b) a coextruded film that has oxygen permeability of below 150 cc/m$^2$.day.bar and that comprises a 4 to 15 $\mu$m thick layer of impermeable material and a 2 to 15 $\mu$m thick layer of a melt-bondable polymeric material on the side of the coextruded film distance from the water-disintegratable film.

Thus in the invention a water-disintegratable film is utilised to give the laminate physical strength and a co-extruded film comprising a layer of impermeable material and a melt bondable layer is utilised to give the laminate impermeability to odour and liquids. By using a co-extruded film it is possible to achieve a reliable and high degree of impermeability to odour and body liquids (due to the presence of the impermeable layer) and to achieve a good edge seal (when this is effected through the co-extruded film) and to have other satisfactory physical properties even though the thickness of the impermeable layer and of the co-extruded film is so low as to minimise or eliminate the risk of blockage during disposal in conventional toilet systems.

The water-disintegratable film must disintegrate in water. Disintegration is fastest if the film will readily dissolve in cold water but a film that dissolves readily only in hot water can be used provided it will swell and disintegrate in cold water. It must be flexible and is normally an embossed film. It can be of any material that is adequately soluble and that will give appropriate reinforcement to the coextruded film. Preferably it has low oxygen permeability when dry. It can be, for instance, of polyethylene oxide but is preferably of polyvinyl alcohol. Polyvinyl alcohols are generally made by hydroylsis from polyvinyl acetate and the degree of hydrolysis affects solubility and other properties. Fully hydrolysed polyvinyl alcohols (e.g., hydrolysed to an extent of at least about 98%) tend to be readily soluble only in warm or hot water. They can be used in the invention but it is preferred to use grades of polyvinyl alcohol which are not quite so fully hydrolysed, as the less hydrolysed grades tend to dissolve more readily in cold water, e.g., 10° to 15° C. Preferably therefore partially hydrolysed polyvinyl alcohol is used, preferably having a degree of hydrolysis from polyvinyl acetate of 70 to 95%, most preferably 73 to 93%.

The water disintegratable film generally has a thickness of at least 20 $\mu$m and usually from 30 to 80 $\mu$m, preferably 30 to 60 $\mu$m, with a thickness of around 40 $\mu$m often being preferred. These thicknesses are suitable especially for polyvinyl alcohol. Lesser thicknesses, e.g. 10 to 40 μm may be suitable, especially for polyethylene oxide.

The co-extruded layer of impermeable material can be of any synthetic polymer that will provide an adequate vapour and gas barrier (despite its thinness) when wet. It can be, for instance, of a copolymer of ethylene and vinyl alcohol but is preferably of a polymer of vinylidene chloride (PVDC). This can be a vinylidene chloride hompolymer or a copolymer with vinyl chloride or methyl acrylate.

The coextruded, melt-bondable, layer can be of any polymeric material that can be coextruded with the impermeable material at the desired thickness and that will provide a layer that can be melt-bonded to secure the laminate to itself or to another surface and that will impart the desired strength and other properties to the coextruded film.

It is preferably formed of an ethylene copolymer. It can be of, for instance, an ethylene-alkyl acrylate copolymer but is preferably of an ethylene vinyl acetate (EVA) copolymer. The EVA will normally have a vinyl acetate content of from 5 to 25%. The layer of EVA or other ethylene polymer preferably has a melt flow index (MFI) of from 0.5 to 7 (expressed as g/10 min and measured at 190° C. according to ASTM-D-1238). The presence of the coextruded layer of EVA or other melt bondable copolymer reduces or eliminates the risk of pinhole porosity that might otherwise exist due to the very low thickness of the PVDC or other impermeable layer and permits effective melt bonding of the laminate. As a result of using a co-extruded film of the two materials, instead of two separate films, the difficulties of producing and handling impermeable, undamaged, very thin films are avoided.

The melt-bondable layer must be exposed and must be on the side of the impermeable layer distant from the water disintegratable layer, in order that it can permit melt bonding. There may be a plurality of melt-bondable layers but generally there is a single melt-bondable layer. Additional, non-interfering, thin layers may be coextruded between the melt-bondable layer and the layer of impermeable material but generally the melt-bondable layer is coextruded in direct contact with the surface of the layer of impermeable material.

The co-extruded film may include layers additional to the layers of impermeable material and of ethylene copolymer. In particular the co-extruded film may include an inner EVA or other ethylene copolymer layer or another inner layer that promotes bonding of the PVDC or other impermeable layer to the water soluble film.

Preferably the total thickness of the co-extruded film is less than 20 μm, generally 10 to 20 μm, and preferably the thickness of the impermeable layer in the co-extruded film is from 5 to 11 μm. The or each melt-bondable layer is generally from 3 to 10 μm.

The oxygen permeability of the co-extruded film material must be below 150 cc/m$^2$.day.bar (measured at 23° C. and 0% R.H.) as otherwise the film will not retain odours adequately. Generally the oxygen permeability is below 100 and preferably it is below 70 cc/m$^2$.day.bar. It is usually above 30 cc/m$^2$.day.bar. The oxygen permeability of the impermeable layer is generally within these limits.

The moisture vapour transmission rate of the coextruded film is generally below 5 g/m$^2$.day (at 38° C. and 100% R.H.).

The oxygen permeability of the total laminate is usually below 50, and often below 30, e.g. 3 to 20, cc/m$^2$.day.bar (23° C., 0% RH).

The co-extruded film can be adhered to the water disintegratable film in any convenient manner. The two films may be formed seperately and the laminated by use of any suitable laminating adhesive. Suitable adhesives for the lamination of films are well known and include polyurethane adhesives, especially two-component adhesives, such as the product sold by Morton Thyocol under the trade name Adcote 710 A and C. The amount of laminating adhesive is usually in the range about 1 to about 15 g/m$^2$, preferably around 5 g/m$^2$.

Instead of using preformed films, the water disintegratable film can be coextruded with the layer of impermeable material and the melt-bondable layer, generally with an adhesion-providing (or tie) layer between the water disintegratable and impermeable layers. Suitable laminates are therefore water disintegratable film/tie layer/ethylene copolymer layer (optional)/impermeable layer/ethylene copolymer layer. Materials that can be used as tie layers are known and include, for instance, modified EVA polymers.

The laminate may include additional layers either between the disintegratable film and the layer of impermeable material or, more usually, on the side of the disintegratable film distant from the impermeable layer, provided any such additional layer does not adversely affect the properties of the laminate. For instance any such layer may be a water-disintegratable film or a biodegradable film. Suitable biodegradable, water-insoluble films are often hydrophilic and may be of cellulosic material. Particularly preferred films are biodegradable, water-insoluble, films of the materials generally known as HB polymers, namely polymers of hydroxy butyric acid alone or with hydroxy valeric acid. HB films that are particularly satisfactory for use in the invention are described in EP-A-0226439.

Preferably any such additional disintegratable or biodegradable film is on the side of the water disintegratable film distant from the layer of impermeable material. It may be bonded over its entire surface area to the water disintegratable film, either by coextrusion or by use of an adhesive layer or both, but it is often preferred that it is spot bonded. The provision of a water-insoluble biodegradable layer over the exposed surface of the water soluble layer is advantageous in that it protects the water soluble layer from body or other moisture and yet the article can still easily disintegrate in water. The use of spot bonding and/or an adhesive that disintegrates in water is advantageous.

It can also be desirable to apply, on the outer side of the water soluble film, a water-degradable non-woven fabric. This is generally bonded to the laminate after the laminate has been manufactured to its final dimensions. The non-woven fabric can be melt-bonded, for instance as a result of a provision of an appropriate melt-bonding layer between the fabric and the water-disintegratable or other adjacent layer or it can be laminated using an appropriate liquid adhesive. The fibres in the fabric are preferably cellulosic and can be bonded, preferably by water soluble or dispersible bonding agent.

The provision of the non-woven fabric allows the production of, for instance, an ostomy bag having an inner face that is impermeable and an outer face that has the softness of non-woven fabric. Suitable non-woven fabrics, fibres, bonding agents and adhesives for this purpose are described in more detail in EP-A-0226439.

The laminates of the invention can be made by conventional coextrusion and lamination techniques and, as is well known, these generally involve stretching extruded films down to the desired thickness. When the laminate is made by bonding a coextruded film with preformed films or other layers, the films will normally have been stretched prior to lamination.

The laminate of the invention can be used in any situation where odour and liquid impermeability but water disposability is required, for instance bedpan liners. However a particular advantage of the invention is that the sheet material can be melt sealed through the ethylene copolymer to another surface to give a very effective and reliable seal, and so the sheet material is of particular value in the production of articles involving melt sealing. Thus it is of value as a diaper backsheet or, especially, in the manufacture of ostomy bags.

A disposable ostomy bag according to the invention is formed of two facing elements of the laminated sheet material with the melt-bondable layer facing inwards and the water disintegratable surface facing outwards, and these elements are melt sealed around their periphery, by the melt-bondable layer, to define the bag. The bag may be formed from two separate elements of the laminate, in which event the melt sealing will extend around the entire periphery, or the bag may be formed from a single laminated sheet that may be folded upon itself, so that part of the periphery is defined by the fold and the remainder of the periphery is melt sealed.

The melt sealing may be effected in conventional manner by impulse heating or, preferably, RF (radio frequency) welding. The ostomy bag may be of conventional construction except for the use of the novel laminated sheet material.

The invention is illustrated in the accompanying drawings, in which

Figure 1:
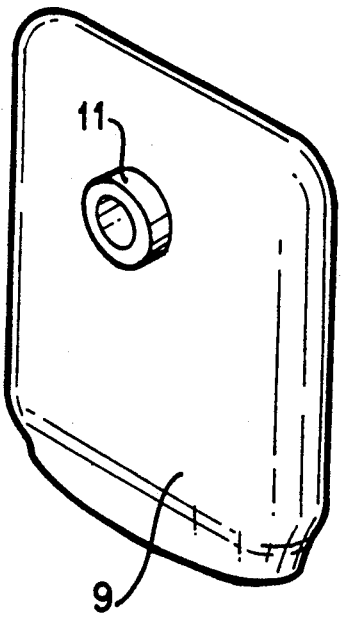
FIG. 1 is a perspective, diagrammatic, view of an ostomy bag.

The ostomy bag of FIG. 1 has conventional overall construction and is formed of a pouch of film material 9 into which is secured a conventional ostomy fitting 11.

Figure 2:
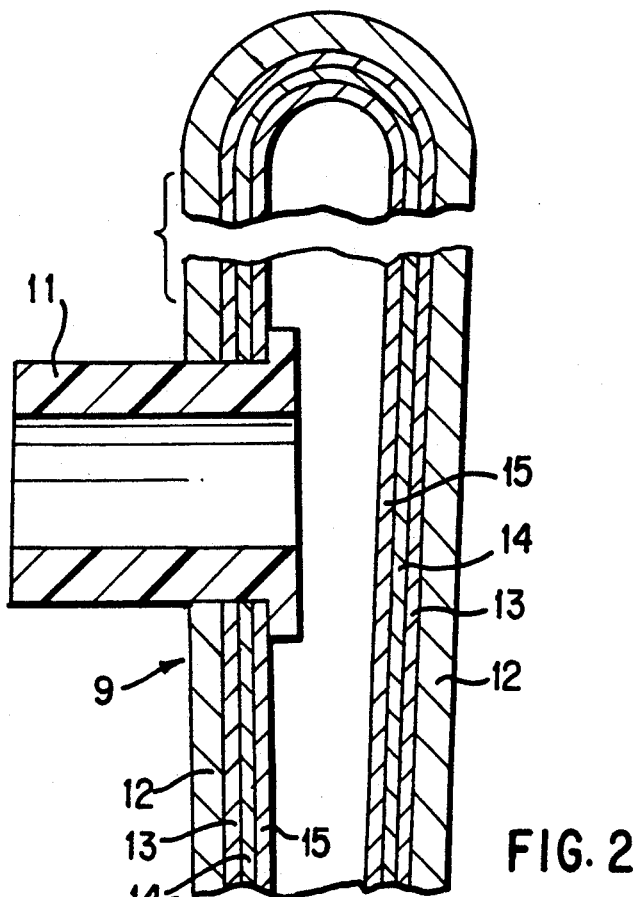
FIG. 2 is a cross section through the bag, the cross section not being to scale and having the thickness of the film components enlarged, for clarity.

A typical bag according to the invention is shown in more detail in FIG. 2, the bag having been formed from film 9 by folding the film into a pouch and melt-sealing the pouch around the facing edges 10 of the film.

In particular, the film 9 may comprise an outer layer 12 of polyvinyl alcohol or other water disintegratable film bonded by an adhesive or tie layer (not shown) to a coextruded laminate of an EVA layer 13, a PVDC layer 14 and an inner EVA layer 15. The melt sealing of the facing layers of the film 9 is conducted through the inner EVA layer 15. The fitting 11 is also melt-sealed utilising the inner EVA layer 15. In a typical laminate the layer 12 is 40 μm thick and the combined thickness of layers 13, 14 and 15 is less than 20 μm.

Figure 3:
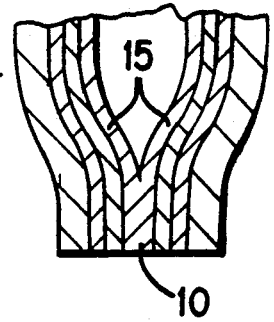
FIG. 3 is a section through a diaper.
Figure 3:
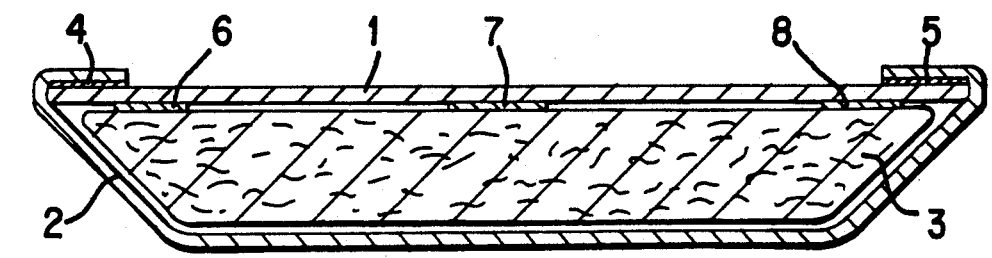

FIG. 3 shows diagrammatically a diaper of conventional construction, comprising a back sheet 1, a permeable, non-woven top sheet 2 and an absorbent pad 3 of cellulosic or other suitable material. The backsheet 1 is, in the invention, formed of a laminate such as the laminate illustrated in FIG. 2, arranged with the polyvinyl alcohol layer 12 facing outwardly and the EVA layer 15 facing inwardly, towards the pad. The backsheet is melt sealed in conventional manner at 4 and 5 to the top sheet and by the layer 15 at 6, 7 and 8 to the pad 3.

The following are some examples of the invention.

EXAMPLE 1

A co-extruded film of 7 μm PVDC and 7 μm EVA was formed in conventional manner by co-extrusion of a laminated tubular film followed by blowing to the desired film thickness. The PVDC was a vinyl chloride vinylidene chloride copolymer and the EVA contained 18% vinyl acetate and had MFI 0.8 (the material from Dupont under the trade name Elvax 3165). The coextruded film had an oxygen permeability of 90 cc/m$^2$.day.bar (23° C., 0% RH).

The PVDC face of this co-extruded film was bonded to an embossed 40 μm film of coldwater soluble polyvinyl alcohol using Adcote 710 A and C at an amount of 5 g/m$^2$. The resultant laminate had an oxygen permeability of 10 cc/m$^2$.day.bar (23° C., 0% RH).

EXAMPLE 2

The process of Example 1 was repeated except that the co-extruded film was formed of a central layer of 9 μm PVDC covered on each surface with a layer of 4 μm EVA. The coextruded film had oxygen permeability of 70 cc/m$^2$.day.bar. and the resultant laminate had an oxygen permeability of 7–8 cc/m$^2$.day.bar (23° C., 0% RH).

EXAMPLE 3

An ostomy bag as illustrated in FIG. 2 can be formed from the laminate of example 2 by RF melt sealing.

It is claimed:

1. A method of making a laminate comprising:
   a) coextruding a film having
      i) a first layer comprising an oxygen impermeable material, and
      ii) a second layer comprising a melt-bondable ethylene copolymer;
   b) adhering to the first layer of the coextruded film a water-disintegratable film; and
   c) adhering a water insoluble layer on the side of the water-disintegratable film distant from the coextruded film.

2. The method of claim 1 further comprising the step of adhering a layer of a melt-bondable ethylene copolymer to the first layer of the coextruded film, prior to adhering the coextruded film to the water disintegratable film.

3. The method of claim 1 wherein the first layer is adhered to the water-disintegratable film by applying a polyurethane adhesive to the water-disintegratable film, and then bringing the coextruded film and water-disintegratable film together.

4. The method of claim 1 wherein the water insoluble layer is adhered to the water-disintegratable film by providing a melt-bonding layer between the water-insoluble layer and the water-disintegratable film.

5. The method of claim 1 wherein the water insoluble layer is adhered to the water-disintegratable film by laminating them together using a liquid adhesive.

* * * * *